(12) United States Patent
Atakan

(10) Patent No.: US 11,732,839 B2
(45) Date of Patent: Aug. 22, 2023

(54) MULTIFUNCTIONAL EQUIPMENT HOLDER

(71) Applicant: Keymed (Medical & Industrial Equipment) Limited, Southend-on-Sea (GB)

(72) Inventor: Nevzat Atakan, Southend-on-Sea (GB)

(73) Assignee: Keymed (Medical & Industrial Equipment) Limited, Southend-on-Sea (GB)

( * ) Notice: Subject to any disclaimer, the term of this patent is extended or adjusted under 35 U.S.C. 154(b) by 0 days.

(21) Appl. No.: 17/479,152

(22) Filed: Sep. 20, 2021

(65) Prior Publication Data
US 2022/0090734 A1 Mar. 24, 2022

(30) Foreign Application Priority Data
Sep. 22, 2020 (GB) ...................... 2014931

(51) Int. Cl.
*F16M 13/02* (2006.01)
*F16B 2/24* (2006.01)
*A61M 25/02* (2006.01)

(52) U.S. Cl.
CPC ........... *F16M 13/022* (2013.01); *F16B 2/243* (2013.01); *A61M 2025/024* (2013.01)

(58) Field of Classification Search
CPC combination set(s) only.
See application file for complete search history.

(56) References Cited

U.S. PATENT DOCUMENTS

| 3,473,768 | A | * | 10/1969 | Piasecki | F16B 21/088 248/68.1 |
| 4,840,345 | A | * | 6/1989 | Neil | F16L 3/12 24/458 |
| 5,314,151 | A | * | 5/1994 | Carter-Mann | B65F 1/06 248/101 |
| 5,772,166 | A | * | 6/1998 | Adams | F21V 21/08 248/229.16 |

(Continued)

FOREIGN PATENT DOCUMENTS

| CN | 102494192 A | 6/2012 |
| CN | 108433815 A | 8/2018 |

(Continued)

OTHER PUBLICATIONS

United Kingdom Intellectual Property Office, Search Report in United Kingdom Patent Application No. GB2014931.6, 1 p. (dated Mar. 19, 2021).

*Primary Examiner* — Monica E Millner
(74) *Attorney, Agent, or Firm* — Leydig, Voit & Mayer, Ltd.

(57) ABSTRACT

An equipment holder comprises a clip with gripping members extending in a first direction. A hook extends from one side of the clip in a second direction. An anchor extends from the opposite side of the clip in a third direction. The clip is configured for releasable engagement with a support structure and with a clip of a like holder. The anchor is configured for releasable engagement with a support structure. The holder can be used in a variety of locations, attached to a support structure by the clip or the anchor. Once holder may also be attached to another holder of the same type for use as a cable management device.

15 Claims, 15 Drawing Sheets

(56) References Cited

U.S. PATENT DOCUMENTS

| | | | |
|---|---|---|---|
| 5,845,883 A * | 12/1998 | Meyer | F16L 3/127 |
| | | | 248/222.12 |
| 5,868,362 A * | 2/1999 | Daoud | H02G 3/26 |
| | | | 248/68.1 |
| 5,893,539 A | 4/1999 | Tran et al. | |
| 5,921,402 A | 7/1999 | Magenheimer | |
| 6,427,952 B2 | 8/2002 | Caveney et al. | |
| 7,140,070 B2 * | 11/2006 | Yuta | B60R 16/0215 |
| | | | 248/74.1 |
| 7,597,296 B2 * | 10/2009 | Conway | G09F 3/20 |
| | | | 52/719 |
| 7,669,807 B2 * | 3/2010 | Stigler | F16B 21/086 |
| | | | 248/231.9 |
| 8,157,222 B1 * | 4/2012 | Shirey | H02G 3/32 |
| | | | 248/68.1 |
| 8,596,588 B1 | 12/2013 | Sikkema et al. | |
| 8,985,530 B2 | 3/2015 | Jette | |
| 9,188,248 B2 | 11/2015 | Kern et al. | |
| D841,451 S | 2/2019 | McGugan | |
| 10,264,736 B2 * | 4/2019 | Rider | A01G 9/12 |
| 10,448,743 B2 * | 10/2019 | Saiga | A47C 7/24 |
| 11,168,836 B2 * | 11/2021 | Kelly | F16B 7/0493 |
| 2001/0030267 A1 | 10/2001 | Caveney et al. | |
| 2015/0086373 A1 | 3/2015 | Kaneko et al. | |
| 2015/0159778 A1 | 6/2015 | Kuhm | |
| 2016/0174719 A1 | 6/2016 | Saiga et al. | |
| 2016/0264030 A1 * | 9/2016 | Saiga | B60N 2/5825 |

FOREIGN PATENT DOCUMENTS

| | | |
|---|---|---|
| DE | 202004010496 U1 | 11/2005 |
| DE | 102017006291 A1 | 1/2019 |
| EP | 1816251 A2 | 8/2007 |

* cited by examiner

MULTIFUNCTIONAL EQUIPMENT HOLDER

CROSS-REFERENCE TO RELATED APPLICATION

This application claims priority to United Kingdom Patent Application No. GB 2014931.6, filed Sep. 22, 2020, which is incorporated by reference herein in its entirety for all purposes.

TECHNICAL FIELD

This patent disclosure relates generally to equipment holders, and, more particularly to the equipment holders that are engagable to another structure.

BACKGROUND

The present invention relates to a multifunctional equipment holder that can be fixed to a variety of different forms of support structure, and can also be connected to another holder of the same configuration for use without a support structure. The holder is particularly useful for retaining elongate, flexible items such as cables, tubes or parts of medical equipment such as endoscopes.

The equipment holder of the present invention is usable in many applications but is especially suitable for use with medical equipment. Medical procedures such as endoscopies require numerous pieces of equipment, typically mounted on a medical workstation comprising a number of shelves mounted on a vertical support structure, which may be in the form of a wheeled trolley. The equipment requires multiple electrical cables and tubing for liquid/gas. There is a need to attach such cables and tubing to the workstation safely and efficiently, ensuring the items are held securely during a medical procedure, but are releasable when required so that the equipment can be cleaned or reconfigured. An equipment holder should be easy to fit the equipment without additional tools, but also easily releasable without causing any damage to the workstation. Various forms of equipment holding clips are known. However, some are not removable, others are only suitable for attachment to a particular geometry of support structure and cannot be used in a variety of different locations or on different equipment, and may require additional tools to fit and remove them. An example of a medical workstation with hooks and clips for attaching other equipment can be found in CN 108433815.

SUMMARY

The present invention provides an equipment holder comprising a clip comprising gripping members which extend in a first direction, a hook which extends from one side of the clip in a second direction and an anchor which extends from the opposing side of the clip in a third direction which is opposite to the second direction, wherein the clip is configured for releasable engagement with a support structure and with a clip of a like holder, and the anchor is configured for releasable engagement with a support structure.

In this way, the present invention provides a versatile and multifunctional holder for the management, routing and retaining of slender flexible equipment such as free-lengths of electrical cables, liquid/gas tubing or medical devices such as endoscopes.

Preferably the clip comprises first and second gripping members defining a slot between them. The first and second gripping members may have proximal ends joined by a base portion and distal ends remote from the base portion, and at least parts of the first and second gripping members may converge towards each other in a direction from proximal ends to the distal ends.

Preferably, the hook and the clip define between them an enclosure for receiving cables/tubes.

The anchor preferably extends from the second gripping member of the clip.

In one embodiment, the anchor is T-shaped and comprises a stem and opposing lateral arms. A notch may be formed in the stem adjacent to the second gripping member.

In another embodiment, the anchor comprises a pair of divergent arms extending from the second gripping member of the clip. The divergent arms may be formed with a plurality of ridges.

In a third embodiment, the anchor comprises a body defining a first anchor slot extending in a direction opposite to the first direction. In this embodiment, the body further defines a second anchor slot extending from the first anchor slot towards the second gripping member of the clip. Preferably, the anchor further defines a tab adjacent to the first anchor slot.

An equipment holder as described above may be provided in combination with a like equipment holder, wherein the holders are releasably engaged together by mutual engagement of the clips of each holder.

Alternatively, an equipment holder of the type comprising a tab and first anchor slot, may be provided in combination with a like equipment holder, wherein the holders are releasably engaged together by mutual engagement of the tab of each holder in the first anchor slot of the other holder.

The equipment holders of the present invention are preferably formed from a resilient material.

BRIEF DESCRIPTION OF THE DRAWING(S)

The invention will now be described in detail, by way of example only, with reference to the accompanying drawings in which.

Figure 1:
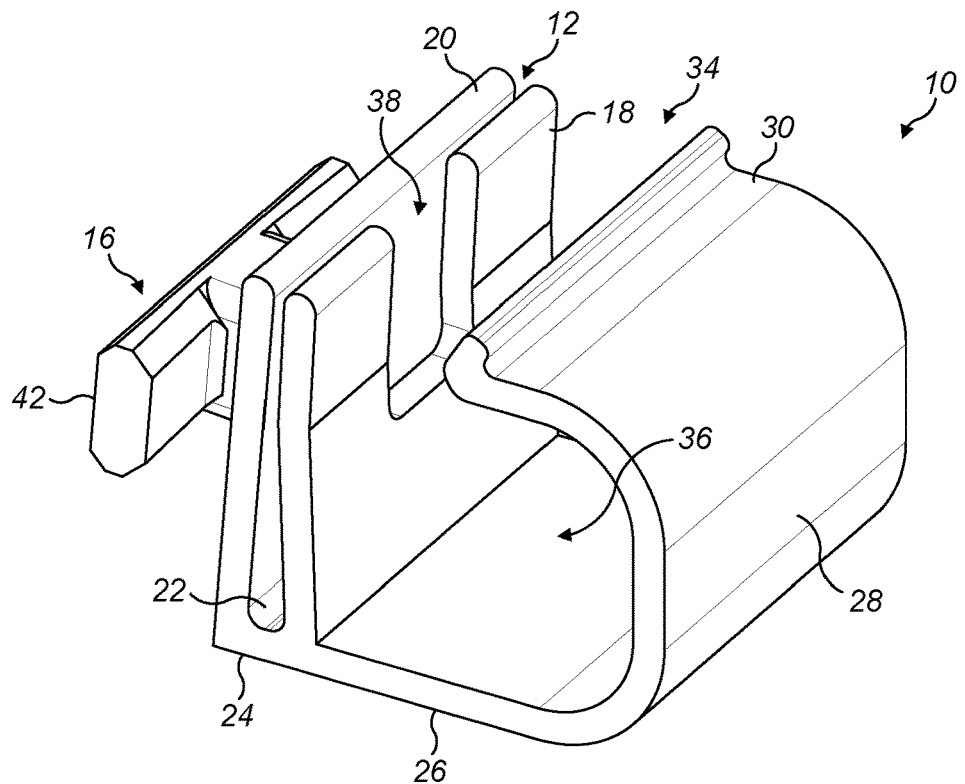
FIG. 1 is a perspective view of a first embodiment of the present invention.
Figure 2:
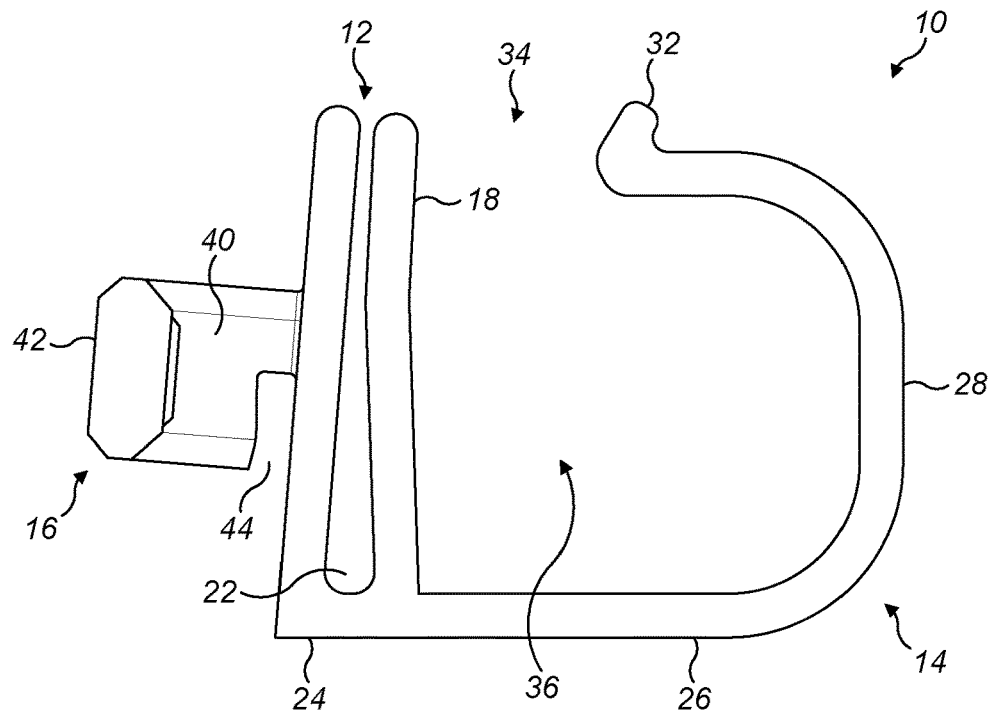
FIG. 2 is a side view of the device of FIG. 1.
Figure 3:
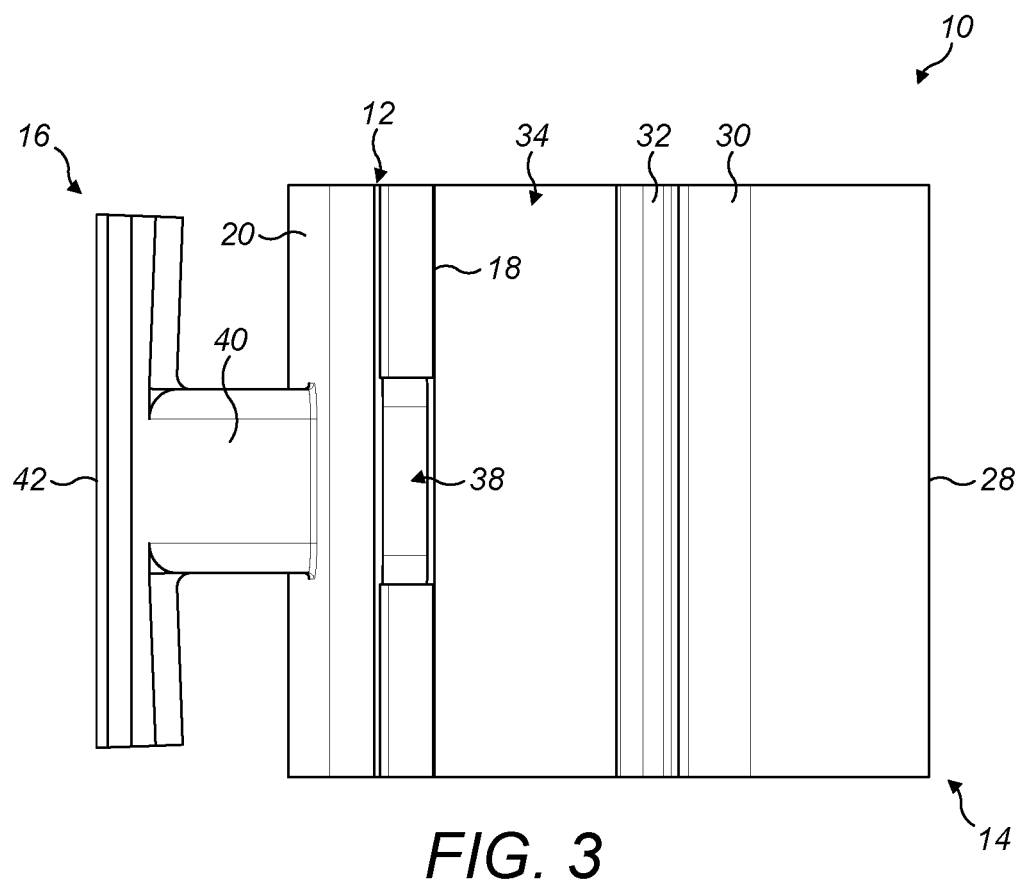
FIG. 3 is a plan view of the device of FIG. 1.
Figure 4:
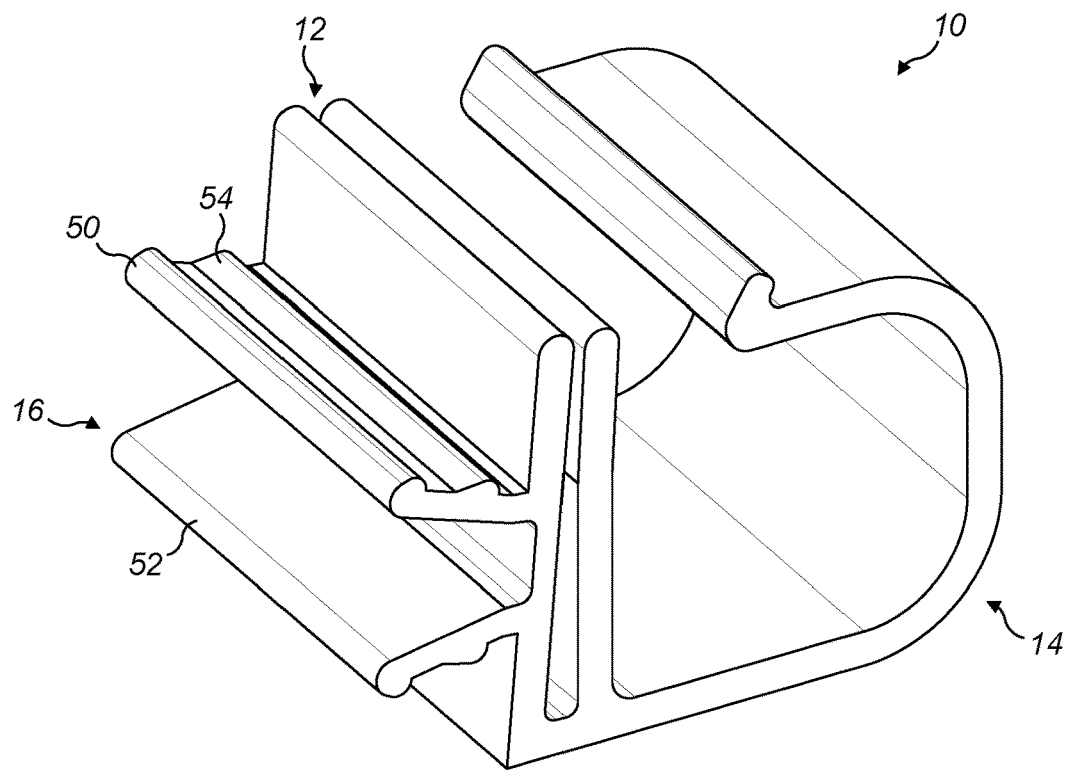
FIG. 4 is a perspective view of a second embodiment of the present invention.
Figure 5:
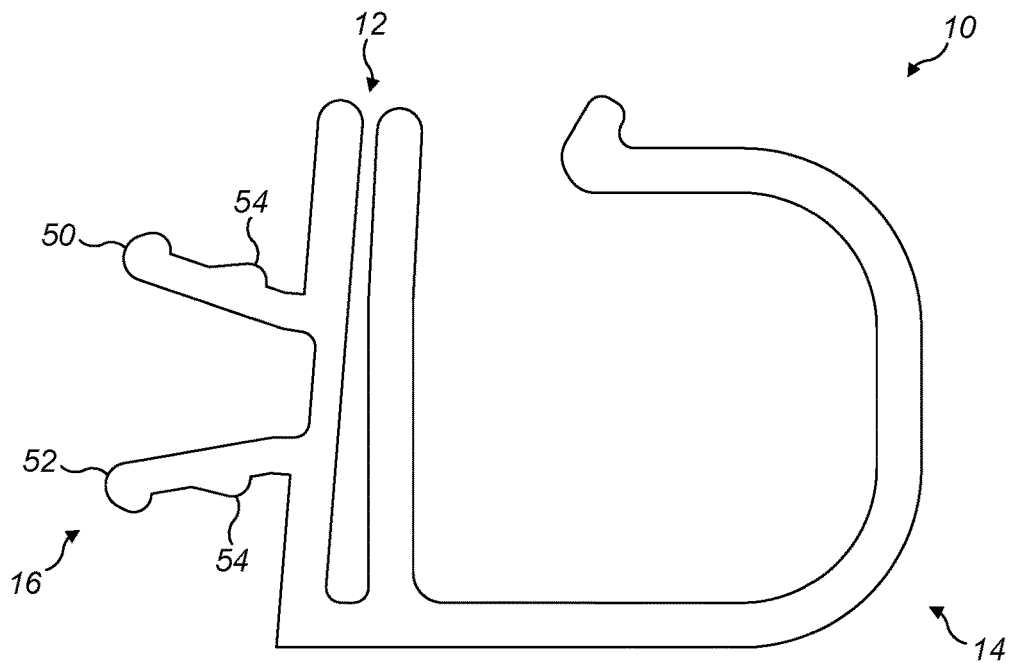
FIG. 5 is a side view of the device of FIG. 4.
Figure 6:
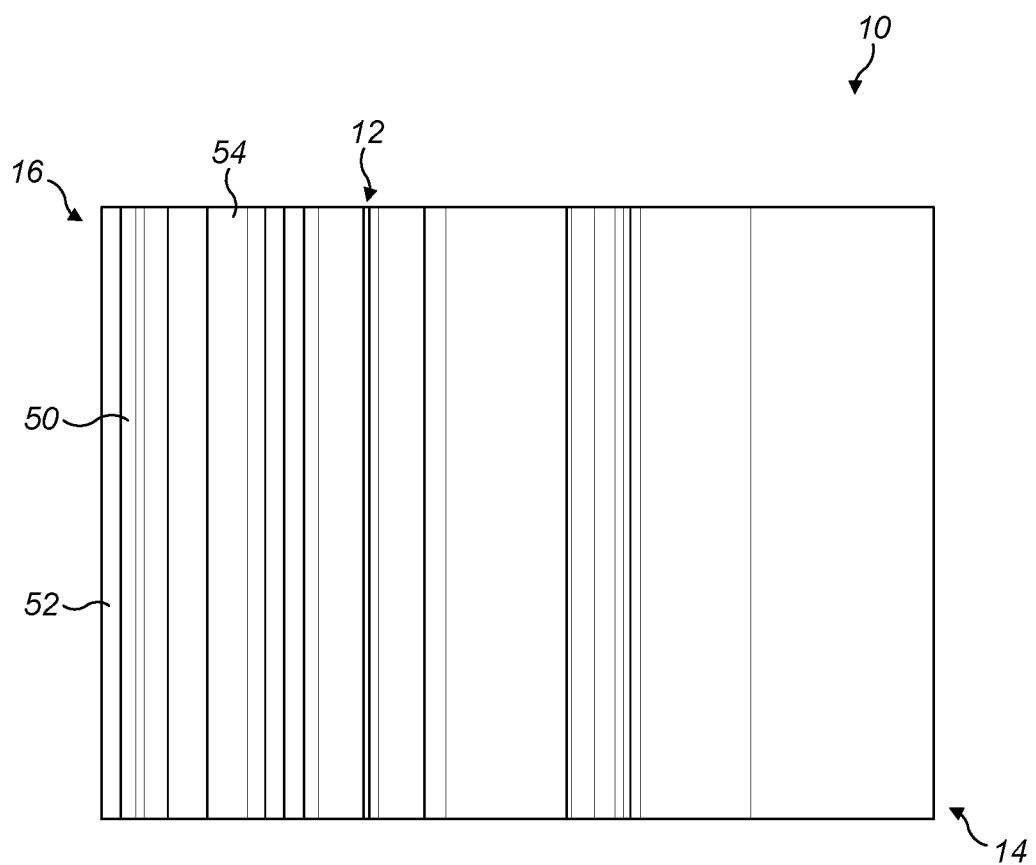
FIG. 6 is a plan view of the device of FIG. 4.
Figure 9B:
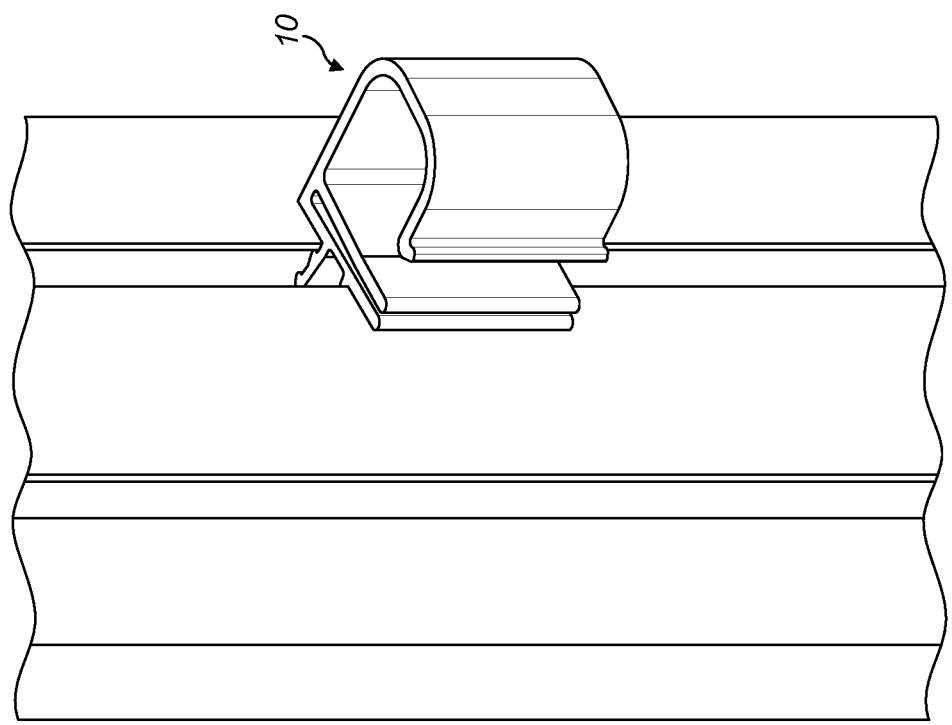
Figure 9A:
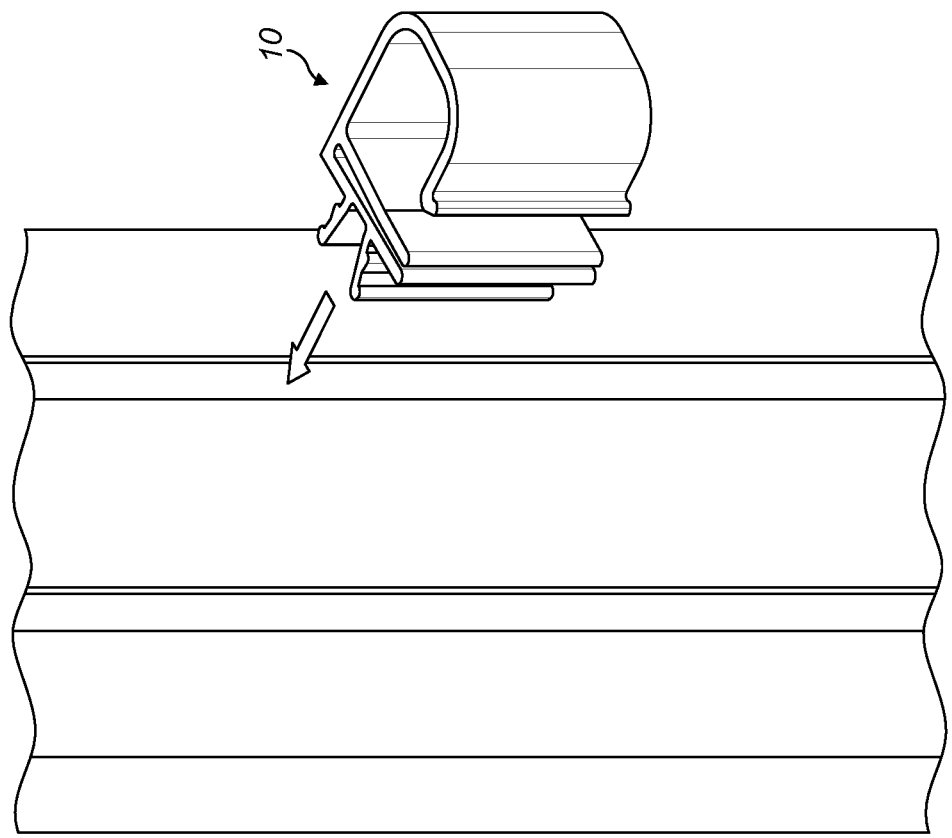
Figure 10:
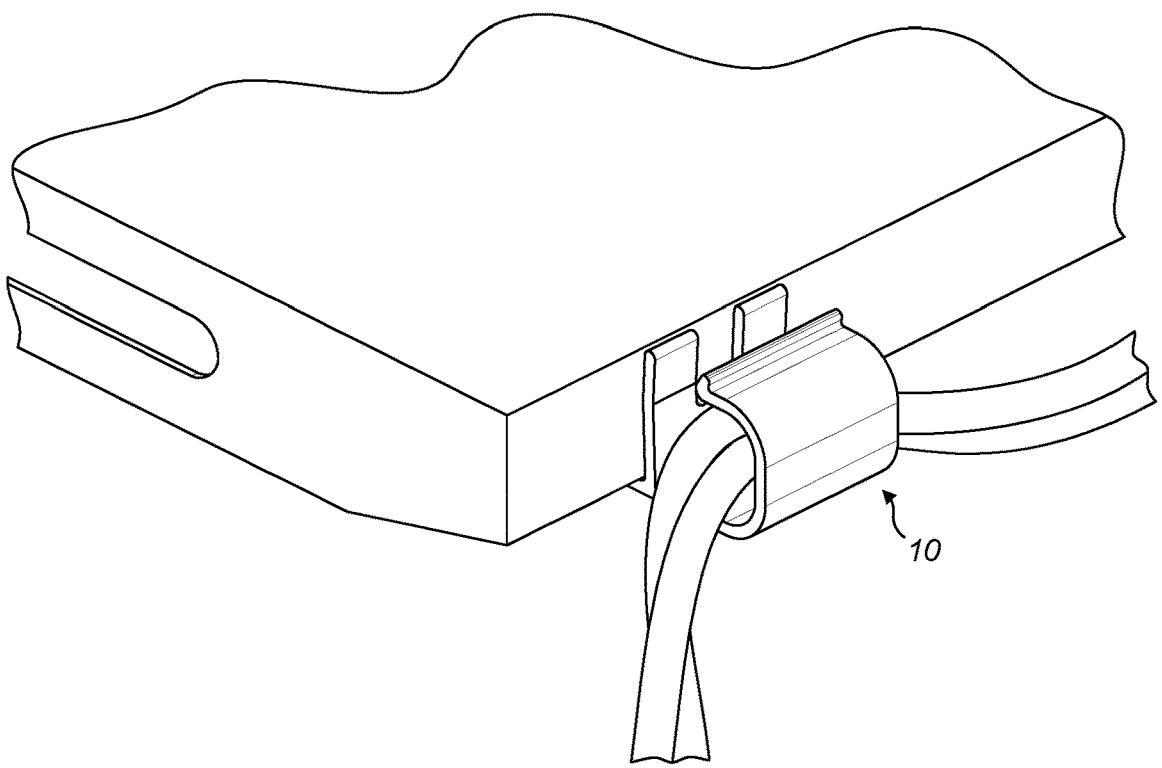
Figure 11:
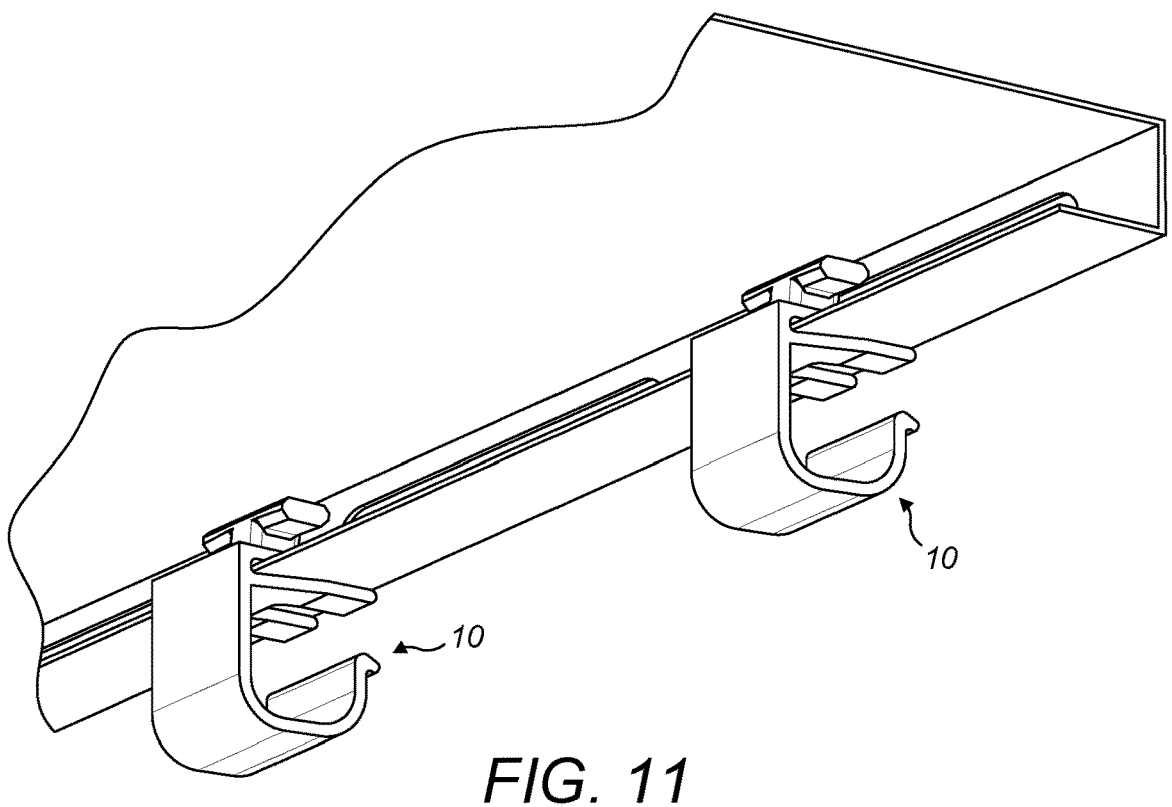
Figure 12:
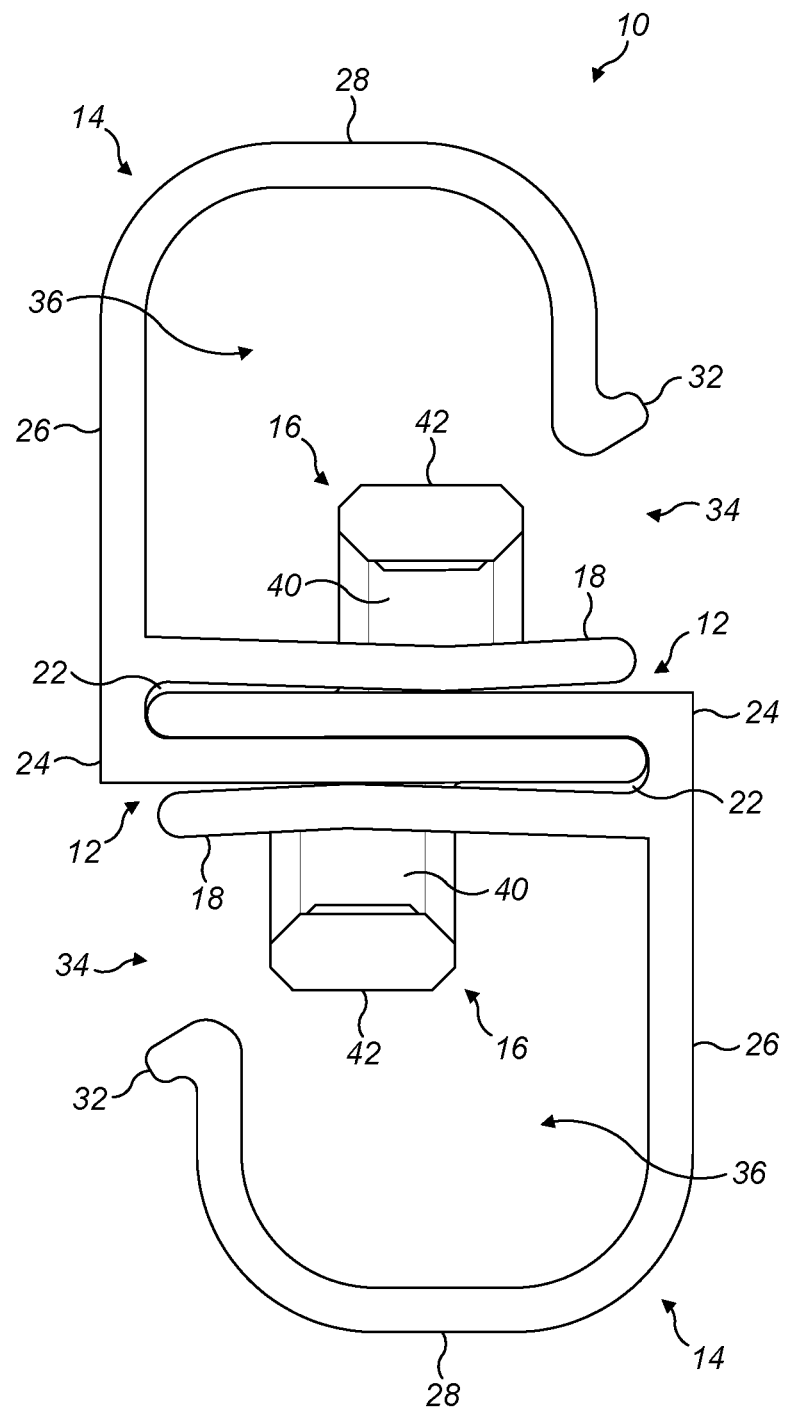

FIGS. 7a-d illustrate connection of the device of FIGS. 1-3 to a support structure with a horizontal slot;

FIGS. 8a-d illustrate connection of the device of FIGS. 1-3 to another form of support structure with a vertical slot;

FIGS. 9a-b illustrate connection of the device of FIGS. 4-6 to the support structure with a vertical slot;

FIGS. 10 and 11 illustrate connection of the device of FIGS. 1-3 to a thin edge of a support structure;

FIG. 12 shows two of the devices of FIGS. 1-3 attached together; and

Figure 13:
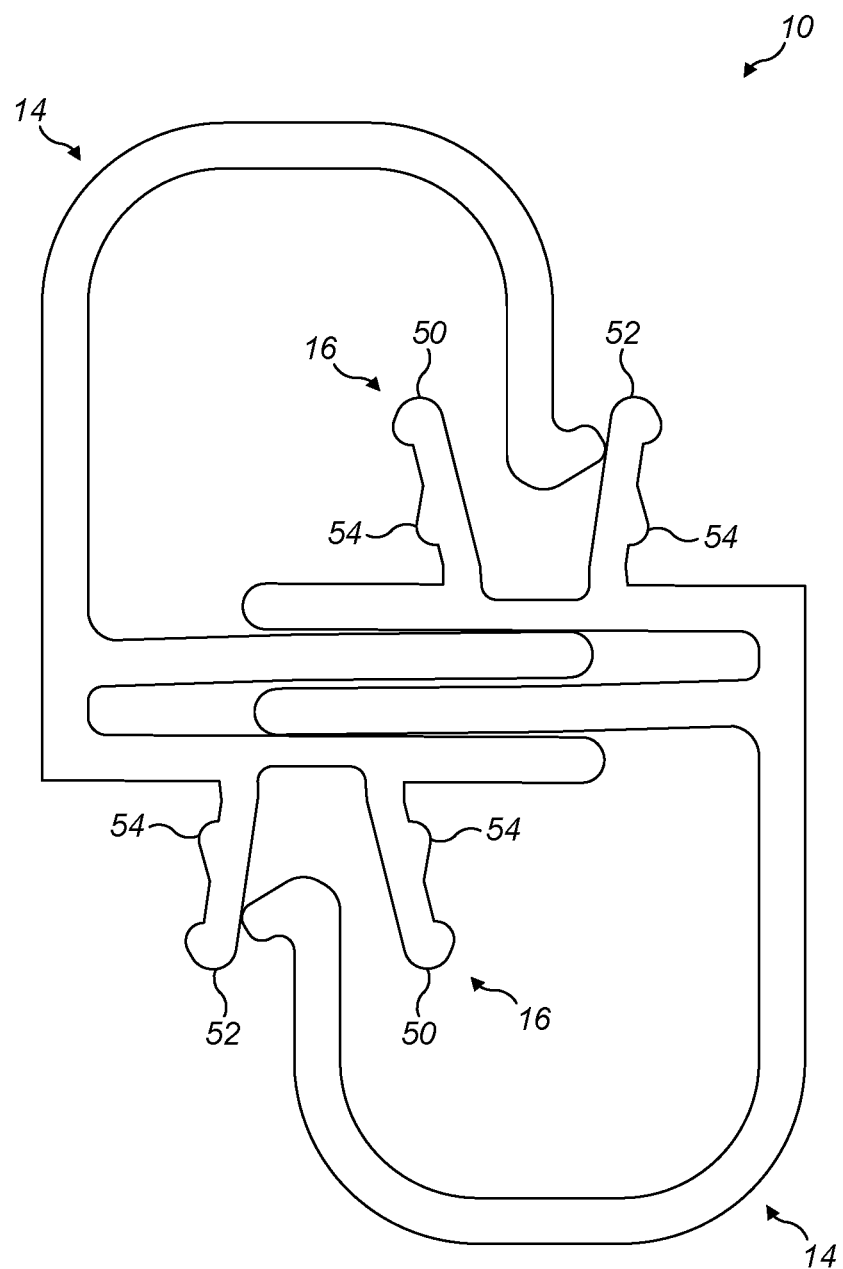
Figure 14:
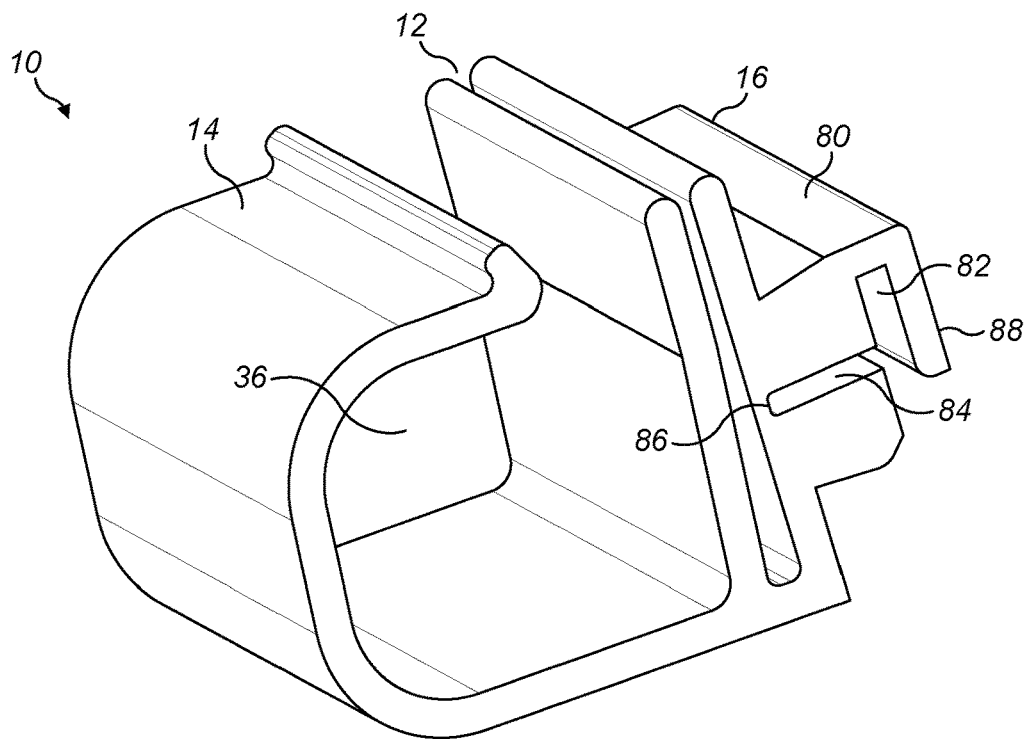
Figure 15:
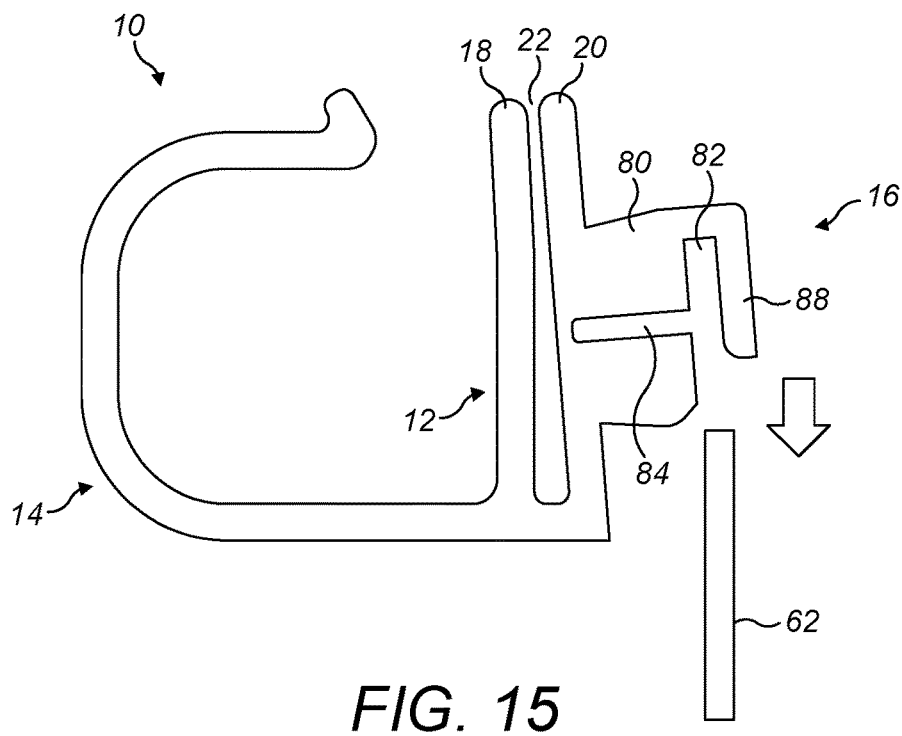
Figure 16:
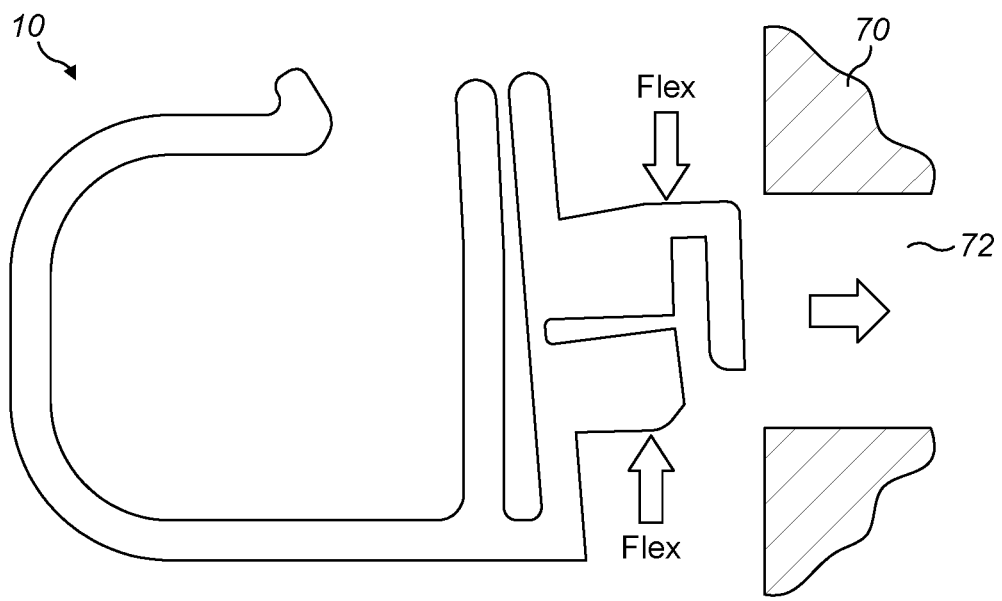
Figure 17:
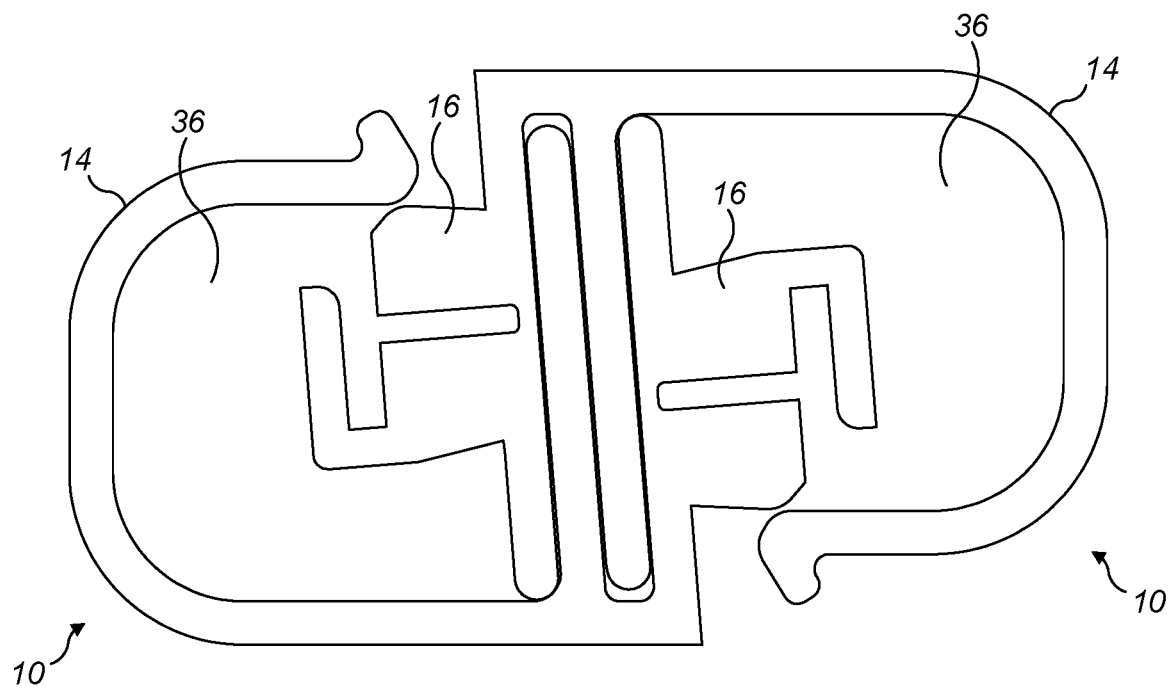
Figure 18:
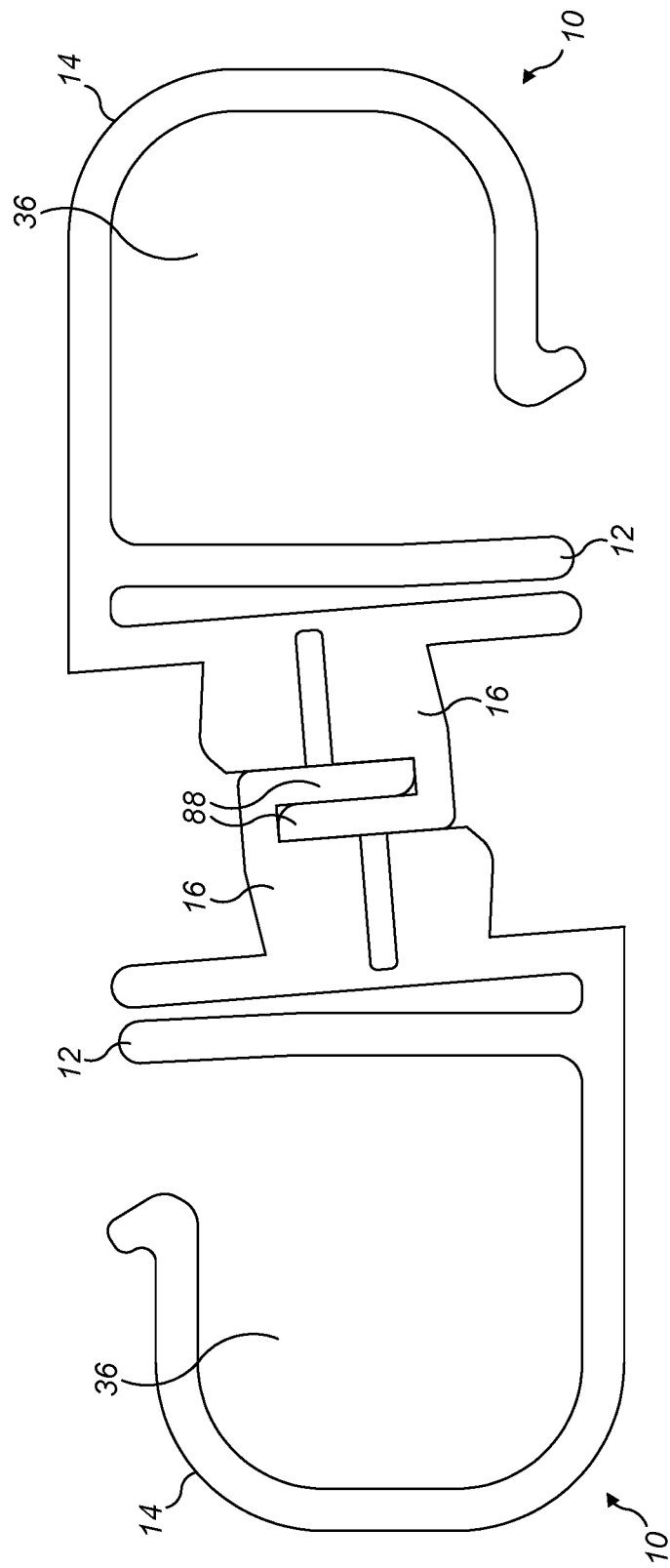

FIG. 13 shows two of the devices of FIGS. 4-6 attached together;

FIG. 14 is a perspective view of a third embodiment of the present invention;

FIG. 15 is a side view of the third embodiment, illustrating fitting onto a thin edge of a support structure;

FIG. 16 is a side view of the third embodiment, illustrating fitting into a slot of a support structure;

FIG. 17 illustrates two of the devices of FIG. 14 attached together in a first configuration; and FIG. 18 illustrates two devices of FIG. 14 attached together in a second configuration.

DETAILED DESCRIPTION

An equipment holder 10 in accordance with the present invention comprises a clip 12, a hook 14 and an anchor 16. The clip 12 comprises gripping members which extend in a first direction. The hook 14 extends from one side of the clip 12 in a second direction. The anchor 16 extends from the other side of the clip 12 in a third direction, which is opposite to the second direction.

A first embodiment of the present invention is illustrated in FIGS. 1-3. In this first embodiment of equipment holder 10, the clip 12 comprises first and second gripping members 18, 20 with a slot 22 between them. The gripping members 18, 20 are joined at the bottom by a base wall 24 so that the clip 12 overall has a generally elongated U-shape. The gripping members 18, 20 extend from the base wall 24 in a first direction (i.e. upwards in FIGS. 1 & 2).

Preferably, at least parts of the gripping members 18, 20 converge towards each other, moving in a direction from the proximal end adjacent base wall 24 towards the distal end. The gripping members 18, 20 may converge over their whole length, or as shown in FIGS. 1 and 2, only the proximal portions of the gripping members 18, 20 may converge, with the distal portions remaining essentially parallel to each other. In its narrowest region, the thickness of the slot 22 is less than the thickness of the gripping members 18, 20.

A hook 14 extends from one side of the clip 12, preferably adjacent to the base wall 24, in a second direction which in this example is generally perpendicular to the first direction in which the gripping members 18, 20 extend away from the base wall 24. Thus, in the orientation of FIGS. 1 and 2 the hook 14 extends to the right hand side. Specifically, the hook 14 comprises a proximal portion 26 extending from the base wall 24 generally perpendicular to the first and second gripping members 18, 20, a mid-portion 28 which turns through 90 degrees to extend up and generally parallel to the gripping members 18, 20, and a distal portion 30 which extends back towards the gripping members 18, 20 and terminates in a turned back distal lip 32. The lip 32 is spaced from the first gripping member 18 of the clip 12, leaving an opening 34 between them allowing access to an enclosure 36 defined by the hook 14 and the first gripping member 18.

A recess 38 is formed in a central, distal portion of the first gripping member 18 as described further below.

The anchor 16 extends from the second gripping member 20 in a third direction, opposite to the second direction in which the hook 14 extends and generally perpendicular to the first direction in which the gripping members 18, 20 extend. Thus, in the orientation of FIGS. 1 and 2 the anchor 16 extends to the left hand side.

In this embodiment, the anchor 16 is substantially T-shaped, comprising a stem 40 extending from the second gripping member 20 and arms 42 extending laterally from the distal end of the stem 40. As shown in FIG. 2, the stem 40 is formed with a notch 44 adjacent to the second gripping member 20.

A second embodiment of the invention is illustrated in FIGS. 4-6. This embodiment is generally the same as the first embodiment as regards the configuration of the clip 12 and hook 14 and therefore these are not described further in detail. However, in the second embodiment, the first gripping member 18 of the clip 12 does not include the recess 38 and the anchor 16 has a different configuration. Specifically, in the second embodiment, the anchor 16 comprises a pair of arms 50, 52 extending from the second gripping member 20.

As seen in FIGS. 4 and 5, the arms 50, 52 diverge from their proximal ends to their distal ends, i.e. from right to left in these Figures. As seen in FIG. 6, the arms 50, 52 are the same width as the clip 12 and hook 14. The lowermost face of the lower arm 52 and the uppermost face of the upper arm 50 are preferably formed with a series of ridges 54.

The holder 10 (of either embodiment) is preferably formed as an integral plastic moulding. This provides a lightweight, cost effective clip that has some innate flexibility and resilience. The configuration of the first embodiment is particularly suitable for injection moulding, while the configuration of the second embodiment is particularly suitable for extrusion.

In use, an equipment holder 10 of the present invention may be used in a variety of different ways. It may be fitted onto a support structure which includes a slot, which may be horizontal or vertical, or it may be fitted onto a thin edge of a shelf or bracket.

Figure 7A:
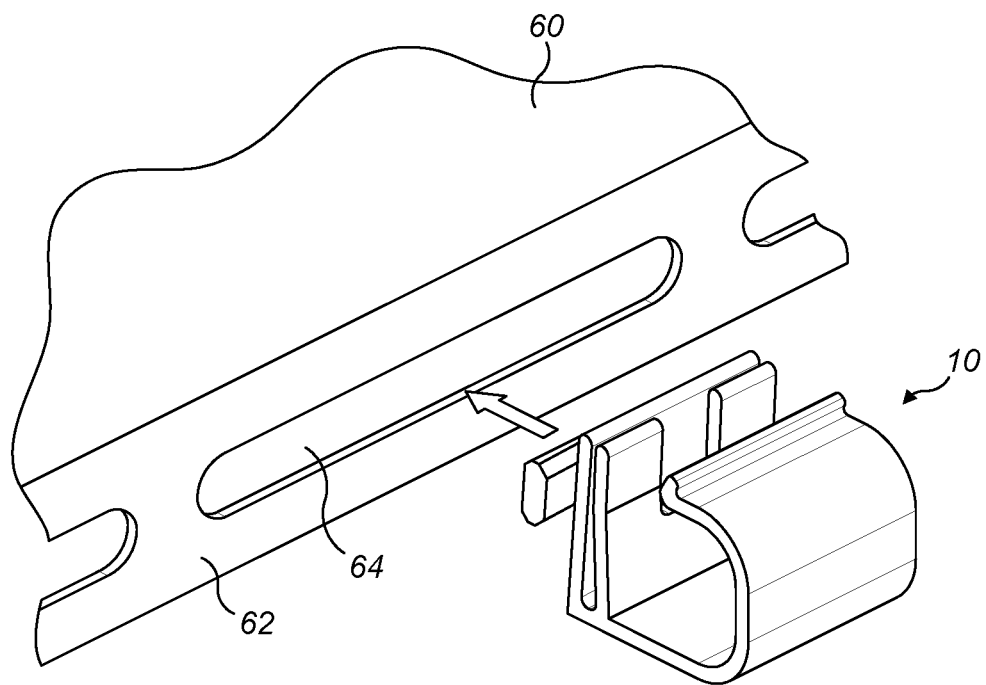
Figure 7B:
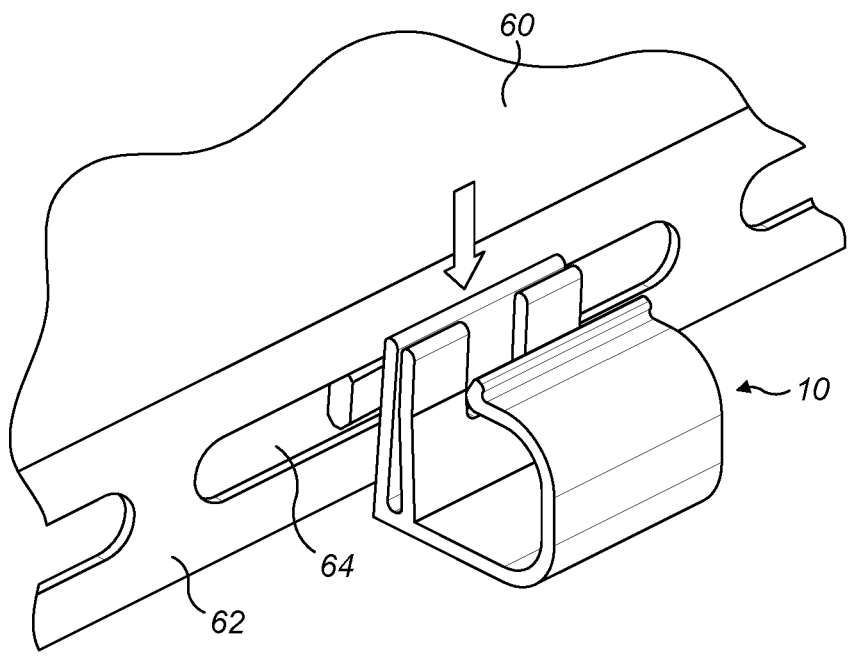
Figure 7C:
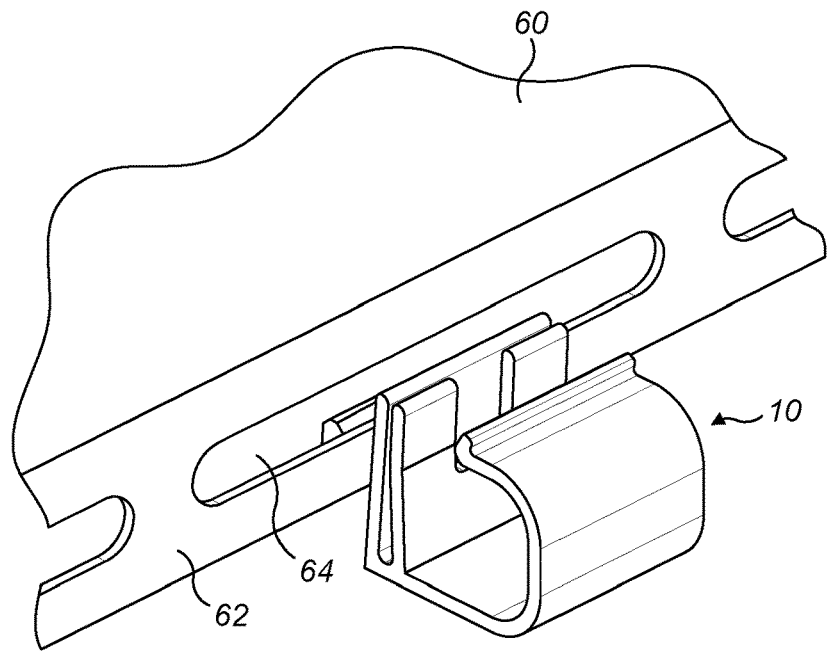
Figure 7D:
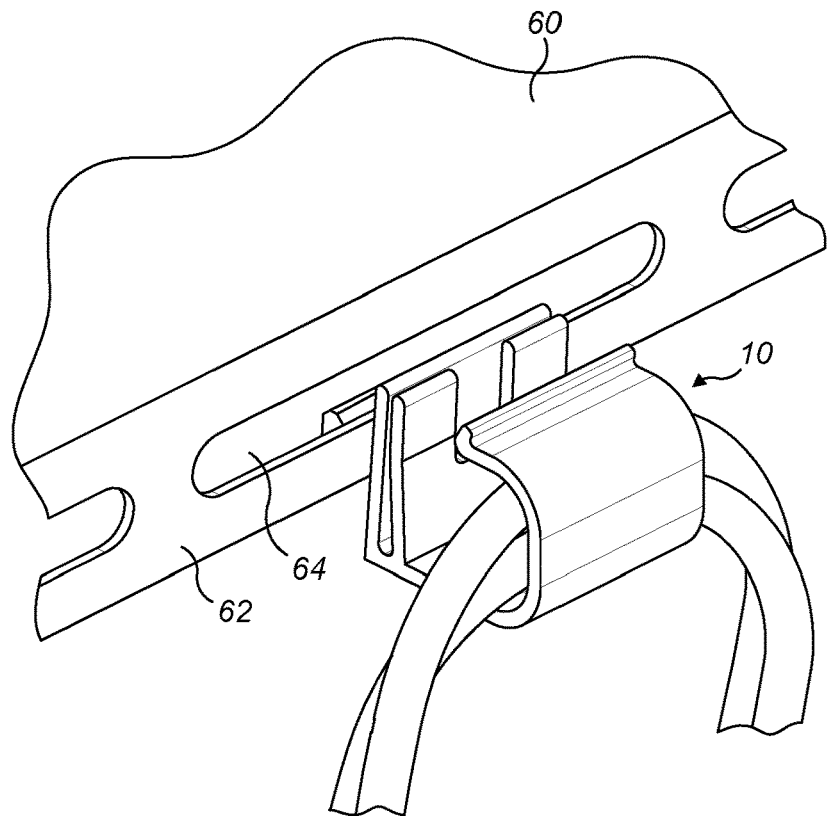

FIGS. 7a-d illustrate a typical shelf 60 made of folded metal providing a vertical side face 62 formed with one or more horizontal apertures 64. A holder 10 of the first embodiment can be fitted to such a shelf 60 by passing the anchor 16 horizontally through the aperture 64 as shown by the arrow in FIG. 7a, and then pushing the holder 10 downwardly as shown by the arrow in FIG. 7b so that the notch 44 in the anchor stem 40 engages over the lower edge of the aperture 64 as shown in FIG. 7c. Once securely fitted, tubing or cables etc. can be threaded through the enclosure 36, or passed into it via the opening 34 to be held by the hook 14 as shown in FIG. 7d.

Figure 8B:
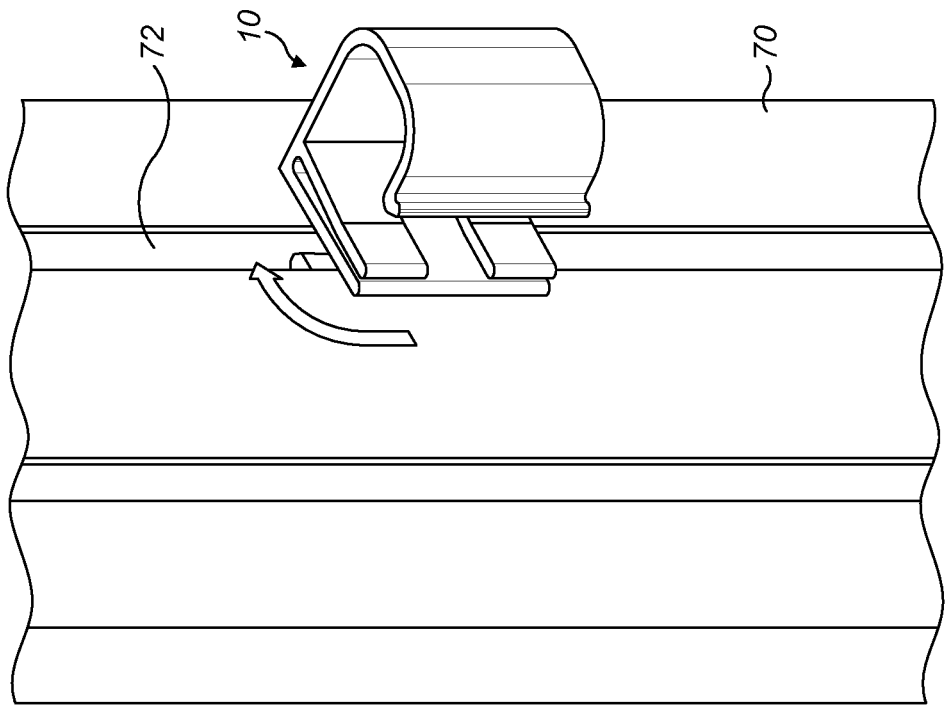
Figure 8A:
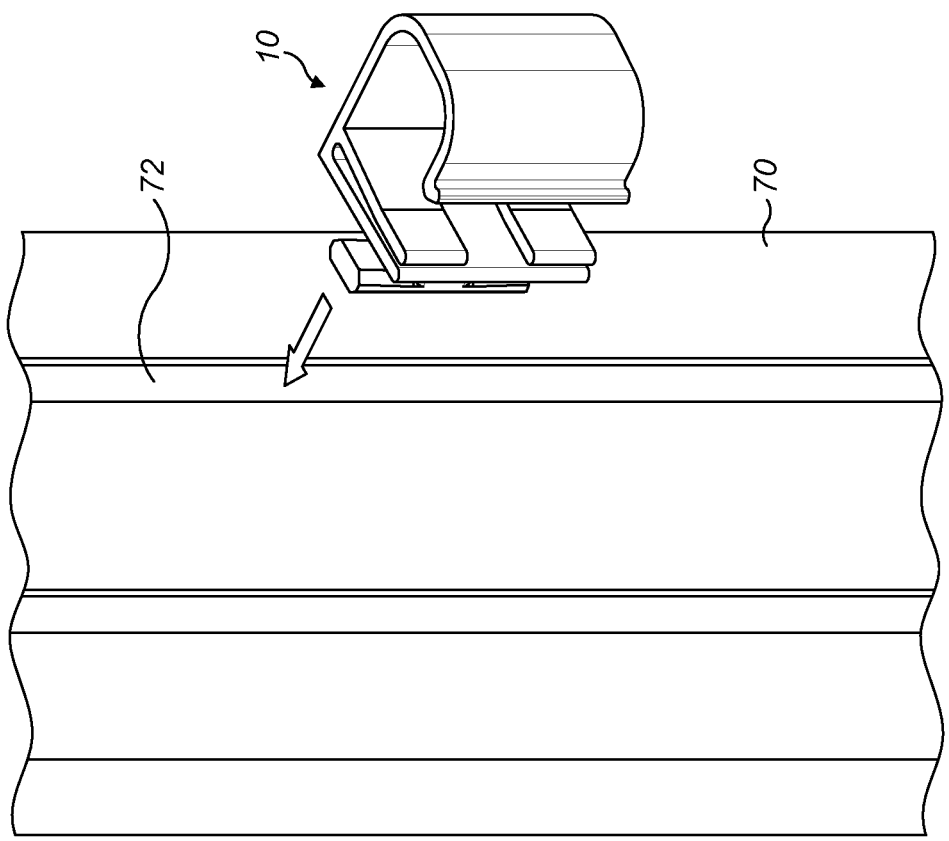
Figure 8D:
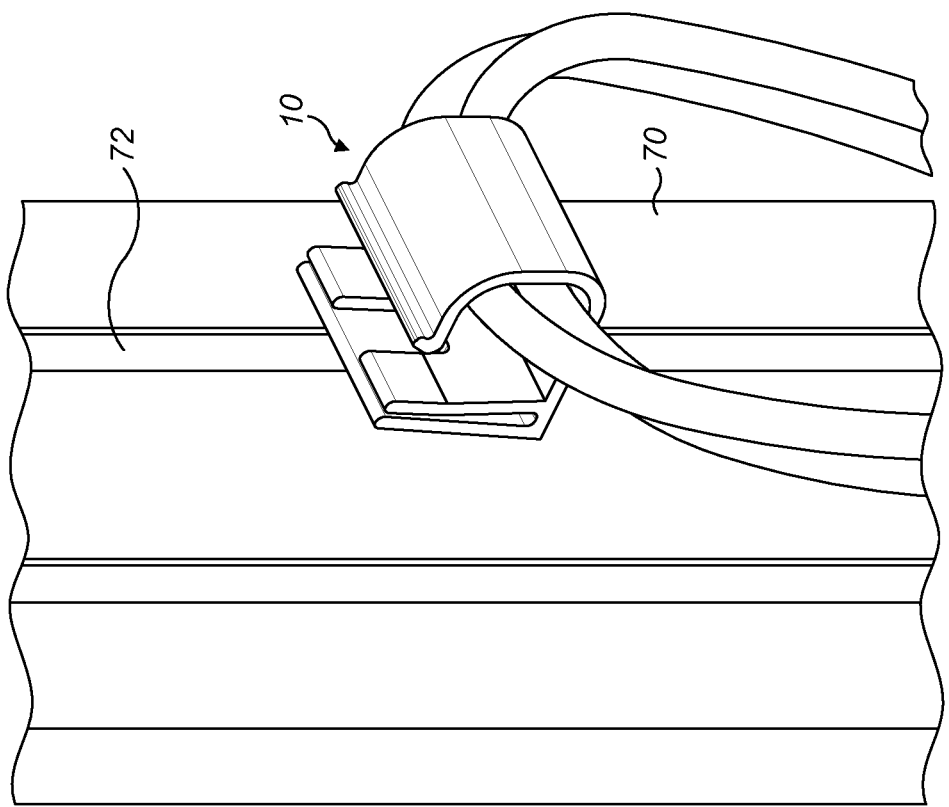
Figure 8C:
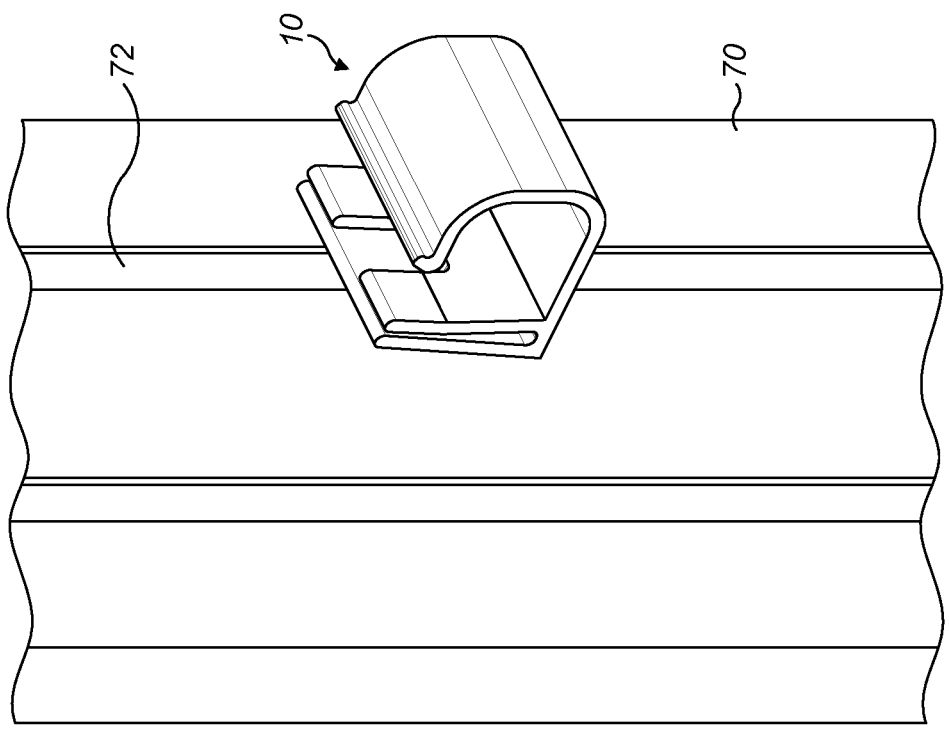

Another form of support structure may be a column 70 (which may be vertical or otherwise in use) with an opening 72 such as a channel defined in the column 70. As shown in FIGS. 8a-d, in this case, a holder 10 in accordance with the first embodiment can be fitted by turning the holder 10 on its side and inserting the anchor 16 through the slot 72 as shown in FIG. 8a, and then rotating the holder 10 through 90 degrees as shown in FIG. 8b until the anchor arms 42 form an interference fit with the internal surfaces of the channel to retain the holder 10 in place as shown in FIG. 8c. Once securely fitted, tubing or cables etc. can be held by the hook 14 as shown in FIG. 8d.

In the case of the second embodiment, this can be fitted into an opening in a support structure by slightly compressing the anchor arms 50, 52 towards each other to allow insertion through the opening. The anchor arms 50, 52 then tend to relax to their divergent state to anchor the holder 10 in place. The ridges 54 on the arms 50, 52 help to resist movement of the holder 10 back out of the opening. In this way a holder 10 of the second embodiment can be fitted to either a horizontal aperture 64 as in FIGS. 7a-d or a vertical opening 72 as in FIGS. 8a-d.

Other forms of support structure may simply provide a horizontal or vertical surface with a thin edge. For example, a shelf may be formed of a flat sheet of metal leaving a thin horizontal edge. Alternatively, sheet metal may be folded down to provide a vertical edge face with a thin edge at the bottom as in FIG. 10. In this case, the clip 12 can be fitted onto the thin edge, with the thin edge slidably received in the slot 22 between the gripping members 18, 20. FIG. 10 shows a holder 10 of the first embodiment but the holder 10 of the second embodiment will function in the same way. Since the gripping members 18, 20 are preferably somewhat convergent and flexible, they can bend apart slightly to accommodate the edge of the shelf as it is inserted and then flex back to grip it. Another form of folded sheet metal shelf is shown in FIG. 11, where the sheet is folded back in under the main shelf surface to leave a thin edge facing inwardly. Again the clip 12 of either embodiment (although the first embodiment is illustrated) can slide on to and grip the edge.

An alternative use for a holder 10 in accordance with the present invention is for tube/cable management independent of a support structure.

As shown in FIGS. 12 and 13, two holders 10 of the same configuration can be fitted together back-to-back by mutual engagement of the clips 12. One holder 10 is inverted relative to the other and the second gripping member 20 of each holder 10 is inserted into the slot 22 of the other holder 10 in order to connect them together.

In the case of the first embodiment, as shown in FIG. 12, the recess 38 on the first gripping member 18 of one clip 12 receives the stem 40 of the anchor 16 of the other holder 10, allowing full insertion of each second gripping member 20 into the corresponding slot 22.

In the case of the second embodiment, as shown in FIG. 13, the second gripping member 20 of a first holder 10 extends only partially into the slot 22 of the second holder 10. The distal end of the hook 14 of one holder 10 is received between the two arms 50, 52 of the second holder 10.

In this way, a cable management device with two enclosures 36 is provided which is useful for holding multiple cables or tubes, or successive turns of a coiled cable or tube, independent of any other support structure. In the back-to-back configuration, parts of the anchor 16 at least partially block the opening 34 into each enclosure 36. This helps to securely retain cables or tubes within the enclosure. However, the inherent resilience of the hook and anchor portions 14, 16 allows some flexing in order to allow cables or tubes to be passed into and out of the enclosures 36 when required.

It will be appreciated that numerous variations of the precise configuration of the holder 10 are possible. For example, FIGS. 14-18 illustrate a third embodiment of equipment holder 10 in which the form of the anchor 16 differs from the first and second embodiments. The clip 12 and the hook 14 of the third embodiment are the same as those described previously and so are not discussed further here. This third embodiment of holder 10 is also suitable for production methods such as extrusion.

In the third embodiment, the anchor 16 comprises a block or body 80 extending from the second gripping member 20 of the clip 12 and formed with two anchor slots 82, 84 which are generally perpendicular to each other. As shown in the side views of FIGS. 15 and 16, the first anchor slot 82 extends generally parallel to the slot 22 formed in the clip 12 but it opens downwardly, while the slot 22 of the clip 12 opens upwardly. In other words, the first anchor slot 82 in the body 80 extends generally in the opposite direction to the direction of the slot 22 in the clip 12. The second anchor slot 84 extends from the first anchor slot 82 towards the clip 12. The second anchor slot 84 extends into the second gripping member 20 of the clip 12 so that the thickness of this gripping member 20 at the base 86 of the slot 84 is slightly reduced. The body 80 may also taper slightly, so that it is narrowest at its proximal end adjacent the clip 12 and increases in width towards its distal end.

The clip 12 of the holder 10 of the third embodiment can be fitted on to a thin edge 62 of a support structure in same way as illustrated in FIGS. 10 and 11. Alternatively, as shown in FIG. 15, the first anchor slot 82 can be fitted onto a thin edge 62 of a shelf of a support structure, in a similar manner to the first embodiment of the invention illustrated in FIGS. 7a-7d.

In addition, as shown in FIG. 16, the anchor 16 of the third embodiment may be inserted into an opening 72 in a support structure 70. In this case, the second anchor slot 84 in the anchor 16 allows the anchor 16 to be squeezed or flexed by pressing on the upper and lower surfaces of the body 80 so that it can be compressed into a narrower configuration in order to pass into the slot 72. Once in place, the anchor 16 tends to expand to its normal state and forms an interference fit with the interior surface of the opening 72, in order to retain the holder 10 in place.

Two of the holders 10 of the third embodiment may also be fitted together in a back-to-back configuration in a similar manner to the first and second embodiments shown in FIGS. 12 and 13. As shown in FIG. 17, one holder 10 is inverted relative to the other and the clips 12 of the two holders 10 mutually engage, with the second gripping member 20 of each clip 12 received in the slot 22 of the other clip 12. In this case, the anchor 16 of each holder 10 is received within the enclosure 36 of the hook 14 of the other holder 10.

An alternative back-to-back configuration is seen in FIG. 18. Formation of the first anchor slot 82 in the body 80 creates a tab 88 at the distal end of the anchor 16. Therefore, with this embodiment two like holders 10 may be connected by inserting the tab 88 of one holder into the first anchor slot 82 of the other holder 10. In this way, the enclosure 36 of each hook 14 is left clear and retains a larger capacity for holding cables, tubes or other equipment.

The present invention therefore provides a multifunctional equipment holder which can be used in a variety of locations. It may be attached to a support structure by gripping an edge or by frictional engagement within an opening. It may also be attached to another holder of the same type for use in cable management, independent of a support structure. A number of configurations are possible all remaining within the scope of the claims.

The invention claimed is:

1. An equipment holder comprising a clip comprising first and second gripping members which extend in a first direction, the first and second gripping members having proximal ends joined by a base portion and distal ends remote from the base portion, and the first and second gripping members defining a slot between them, a hook which extends from the proximal end of the first gripping member adjacent to the base portion and in a second direction generally perpendicular to the first direction, and an anchor which extends from the second gripping member between the proximal and distal ends and spaced from the base portion and in a third direction which is opposite to the second direction and generally perpendicular to the first direction, wherein the clip is configured for releasable engagement with a support structure and with a clip of a like holder, and the anchor is configured for releasable engagement with a support structure.

2. An equipment holder as claimed in claim 1, wherein at least parts of the first and second gripping members converge towards each other in a direction from proximal ends to the distal ends.

3. An equipment holder as claimed in claim 1, wherein the hook and the clip define between them an enclosure for receiving cables, tubes or other equipment.

4. An equipment holder as claimed in claim 1, wherein the anchor extends from the second gripping member of the clip.

5. An equipment holder as claimed in claim 4, wherein the anchor is T-shaped and comprises a stem and opposing lateral arms.

6. An equipment holder as claimed in claim 5, wherein a notch is formed in the stem adjacent to the second gripping member.

7. An equipment holder as claimed in claim 1, wherein the anchor is compressible to a narrower configuration for insertion into an opening support structure and expandable into a larger configuration for frictional engagement within the opening.

8. An equipment holder as claimed in claim 7, wherein the anchor comprises a pair of divergent arms extending from the second gripping member of the clip.

9. An equipment holder as claimed in claim 8, wherein the divergent arms are formed with a plurality of ridges.

10. An equipment holder as claimed in claim 4, wherein the anchor comprises a body defining a first anchor slot extending in a direction opposite to the first direction.

11. An equipment holder as claimed in claim 10 wherein the body further defines a second anchor slot extending from the first anchor slot towards the second gripping member of the clip.

12. An equipment holder as claimed in claim 10, wherein the anchor further defines a tab adjacent to the first anchor slot.

13. An equipment holder as claimed in claim 1, in combination with a like equipment holder, wherein the holders are releasably engaged together by mutual engagement of the clips of each holder.

14. An equipment holder as claimed in claim 12, in combination with a like equipment holder, wherein the holders are releasably engaged together by mutual engagement of the tab of each holder in the first anchor slot of the other holder.

15. An equipment holder as claimed in claim 1, formed from a resilient material.

* * * * *